United States Patent [19]

Konstantinov et al.

[11] Patent Number: 5,597,700
[45] Date of Patent: Jan. 28, 1997

[54] METHOD FOR DETECTING FREE INSULIN-LIKE GROWTH-FACTOR-BINDING PROTEIN 1 AND A TEST DEVICE FOR DETECTING THE RUPTURES OF FETAL MEMBRANES USING THE ABOVE METHOD

[75] Inventors: Alexander Konstantinov, Princeton, N.J.; Boris Foux, Moscow, Russian Federation; Alexander Stepanov, Moscow, Russian Federation; Evgeny Zaraisky, Moscow, Russian Federation; Svetlana Nazimova, Moscow, Russian Federation; Marina Boltovskaya, Moscow, Russian Federation; Nelli Starosvetskaya, Moscow, Russian Federation

[73] Assignee: California Research, LLC, Mountain View, Calif.

[21] Appl. No.: 234,851

[22] Filed: Apr. 28, 1994

[51] Int. Cl.[6] .................................... G01N 33/53
[52] U.S. Cl. .................. 435/7.92; 435/794; 435/967; 435/969; 435/970; 436/518; 436/530; 436/810; 422/56; 422/58; 422/60; 530/388.24
[58] Field of Search ..................... 435/7.9, 7.92, 435/7.94, 805, 967, 969, 970; 436/518, 530, 810; 422/56, 58, 60; 530/388.24

[56] References Cited

U.S. PATENT DOCUMENTS

| 4,235,601 | 11/1980 | Deutsch et al. | 435/7.92 |
|---|---|---|---|
| 4,861,711 | 8/1989 | Friesen et al. | 422/56 X |
| 4,981,786 | 1/1991 | Dafforn et al. | 422/58 X |
| 5,006,474 | 4/1991 | Horstman et al. | 436/524 |
| 5,120,643 | 6/1992 | Ching et al. | 435/7.92 |
| 5,308,775 | 5/1994 | Donovan et al. | 436/518 |

FOREIGN PATENT DOCUMENTS

| 2204398 | 9/1988 | United Kingdom | 422/58 |
|---|---|---|---|
| 2239313 | 6/1991 | United Kingdom . | |
| WO92/12426 | 7/1992 | WIPO | 435/7.1 |
| WO94/00765 | 1/1994 | WIPO . | |

OTHER PUBLICATIONS

C. Lockwood et al, "Fetal membrane rupture is associated with the presence of insulin–like growth factor–binding protein–1 in vaginal secretions," in *Am. J. Obstet. Gynecol.* 171(1):146–150 (Jul. 1994).

Chemical Abstract 119(11):109213, "Localization of the epitope of a monoclonal antibody against human insulin–like growth factor binding protein–1, functionally interferring with insulin–like growth factor binding," by Schuller et al. in Growth Reg. 1993, 3(1), 32–34.

P. Hellemans et al., Preliminary results with the use of the ROM–check immunoassay in the early detection of rupture of the amniotic membranes, Eur. J. Ob. & Gyn and Repro. Biol. 43 (1992) 173–179.

(List continued on next page.)

*Primary Examiner*—Carol A. Spiegel
*Attorney, Agent, or Firm*—Susan T. Evans; Peter J. Dehlinger; David Pressman

[57] ABSTRACT

A method and device for detecting fetal membrane rupture by detecting only that insulin-like growth-factor-binding protein 1 (IGFBP-1) which is free of insulin-like growth factors 1 and 2 (IGF-1 and IGF-2) are disclosed. The method is based on the fact that the concentration of free IGFBP-1 in the blood serum is about 10 times lower than that of the IGFBP-1 bound to IGF-1 and IGF-2, while in the amniotic liquid which is contained in the amnion has more than 1000 times the concentration of free IGFBP-1 than the blood serum. Therefore, when even a small amount of amniotic liquid is contained in the vaginal secretion sample, this is clear evidence of the rupture of the fetal membrane having taken place. The method and the device make it possible to diagnose fetal membrane rupture with an extremely high accuracy. Because of the low concentration of the IGFBP-1 in the blood, the admixture of the blood serum to the sample does not affect the results of the test. The device comprises a one-pad-two-strips test kit which may be used to detect free IGFBP-1 in a range of concentrations from 5 ng/ml to 250 μg/ml.

6 Claims, 9 Drawing Sheets

OTHER PUBLICATIONS

M. L. Friedman et al., Diagnosis of ruptured fetal membranes, Am. J. Obst. & Gynec, Jun. 1969, pp. 544–550.

G. Póvoa et al., Cross–reaction of serum somatomedin–binding protein in a radioimmunoassay developed for somatomedin–binding protein isolated from human amniotic fluid, Acta Endrocrinologica 1984, 107:563–570.

S. C. Hodgkinson et al., Metabolic clearance rate of insulin–like growth factor–I in fed and starved sheep, J. Endroc. (1987) 115,233–240.

F. Pekonen et al., A monoclonal antibody–based immunoradiometric assay for low molecular weight insulin–like growth factor binding protein/placental protein 12, J. Immunoassay, 10(4), 325–337 (1989).

H. Bohn et al., Isolation and Characterization of a New Placenta Specific Protein ($PP_{12}$), Arch. Gynecol 229, 279–291 (1980). English abstract only.

E. Rutanen et al., Measurement of insulin–like growth factor binding protein–1 in cervical/vaginal secretions: comparison with the ROM–check Membrane Immunoassay in the diagnosis of ruptured fetal membranes, Clinica Chimica Acta 214 (1993) 73–81.

P. R. Koninckx et al., Prolactin concentration in vaginal fluid: a new method for diagnosing ruptured membranes, Brit. J. Ob. Gyn., Jun. 1981, 88:607–610.

C. J. Lockwood et al., Fetal fibronectin in cervical and vaginal secretions as a predictor of preterm delivery, N.E.J. Med, 1991 Sep. 5, pp. 669–674.

B. L. Rochelson et al., Rapid assay—possible application in the diagnosis of premature rupture of the membranes, Ob. and Gyn, 62:414–418 (Oct. 1983).

B. L. Rochelson et al., A rapid colorimetric AFP monoclonal antibody test for the diagnosis of preterm rupture of the membranes, Ob. and Gyn, 69:163–165 (Feb. 1987).

R. Koistinen et al., Placental protein 12 is a decidual protein that binds somatomedin and has an identical N–terminal amino acid sequence with somatomedin–binding protein from human amniotic fluid, Endocrinology, 118:1375–1378 (1986).

M. J. N. C. Keirse et al., 43. Prelabour rupture of the membranes pretrem, Effective Care In Pregnancy And Childbirth, Oxford U. Press, 1989, pp. 666–693.

M. Roghani et al., Two insulin–like growth factor (IGF)–binding proteins are responsible for the selective affinity for IGF–II of cerebrospinal fluid binding proteins, J. Clin. Endro & Metabolism, 73:658–666 (1991).

S. C. Bell et al., N–terminal amino aid sequence of human pregnancy–associated endometrial $\alpha_1$–gobulin, an endometrial insulin–like growth factor (IGF) binding protein –evidence for two small molecular weight IGF binding proteins, Endocrinology, (1988) vol. 123, pp. 1202 to 1204.

R. P. Smith, A Technic for the Detection of Rupture of the Membranes, Obstetrics and Gynecology, pp. 172–176, Aug. 1976.

D. D. Petrunin et al., Immunochemical Identification Of Organospecific $\alpha_1$—gobulin Of A Human Placenta And Its Content In Amniotic Liquid, Obstretrics and Gynecology, Moscow, published by "Meditsina", 1977, Nr. 1, pp. 64–65. No English Translation.

M. N. Boltovskaya et al., Histochemical and Clinico–Diagnostiocal Study Of The Placental Alpha–I–Microgobulin (PAMG–1) Using Monoclonal Antibodies, Bulletin Of Experimental Biology And Medicine, USSR, Nr. 7, 1991, pp. 397–400. No English Translation.

Waites, G. T., et al., "Human 'prenancy–associated endometrial $\alpha_1$-globulin', an insulin–like growth factor–binding protein: immunohistological localization in the decidua and placenta during pregnancy employing monoclonal antibodies," J. Endocrinol. 120:351–357 (1989).

Rutanen, E.–M., et al., "Monoclonal Antibodies To The 37–34K Insulin–Like Growth Factor Binding Protein," Biochem. and Biophys. Res. Communications 152:1:208–215 (1988).

Bell, S. C., et al., "Monoclonal Antibodies to Human Secretory 'Pregnancy–Associated Endometrial $\alpha_1$–Globulin,' An Insulin–Like Growth Factor Binding Protein: Characterization and Use in Radioimmunoassay, Western Blots, and Immunohistochemisty," AJRI (American Journal of Reproductive Immunology) 20:3:87–96 (Jul. 1989).

METHOD FOR DETECTING FREE INSULIN-LIKE GROWTH-FACTOR-BINDING PROTEIN 1 AND A TEST DEVICE FOR DETECTING THE RUPTURES OF FETAL MEMBRANES USING THE ABOVE METHOD

BACKGROUND—FIELD OF THE INVENTION

The present invention relates to the field of medicine, particularly to a diagnostic method for detecting free, i.e., unbound, insulin-like growth factor-binding protein 1 (hereinafter referred to as free IGFBP-1), and to a test device for detecting the ruptures of fetal membranes using the above method.

BACKGROUND—DESCRIPTION OF THE PRIOR ART

According to statistical data, the premature rupture of the fetal membrane (the amniotic sac) occurs in about 5 to 14% of pregnant women and is the cause of about 10% of all perinatal deaths. More than 30% of such premature ruptures of fetal membranes occur before 37 weeks of pregnancy. In such cases, the diagnosis of rupture is extremely important because the rupture of the membrane is associated with significant increases in the risk of an intrauterine infection, Keirse M. J. N. C., et al., "Prelabor Rupture of the Membranes Preterm," in *Effective Care in Pregnancy and Childbirth,* 1989, vol. 1, Oxford, New York, Toronto. Edited by J. Chalmers, M. Enkin, and M. Keirse.

The risk of intrauterine penetration of infection increases significantly as time passes between the rupture of the membranes and the delivery. Penetration of infection increases both maternal and perinatal mortality. When rupture occurs at the end of pregnancy, delivery should be effected as soon as possible. Therefore, a positive diagnosis of rupture at this period (38–40 weeks of pregnancy) is especially important. On the other hand, a positive diagnosis is equally important before 34 weeks of pregnancy, since it permits the timely monitoring and treatment of pregnant women to prevent intra-amnion infection and to stimulate fetal lung development.

One of the methods used at the present time to diagnose the rupture of the fetal membrane is a so-called crystallization test which is described by M. L. Friedman and T. W. McElvin in the *American Journal of Obstetrical Gynecology,* 1969, vol. 104, pp. 544–550. This method is based on detection of the presence of amniotic fluid in vaginal secretions and the observation of arborization, i.e., the formation of a tree-branch-like structure, which occurs when the amniotic fluid dries on a slide.

Amniotic fluid is a transparent, almost colorless fluid contained within the amniotic sac surrounding the fetus. It is composed of many proteins and other substances. When the fetal membrane ruptures, the visual image resulting from the aforementioned tree-branch-like structure should differ from that which results from normal vaginal secretions.

This method, however, is not accurate. In as many as 30% of the cases, it produces false results because the pattern which is assumed to be normal often overlaps with that which in fact corresponds to the case of the ruptured fetal membrane, and vice versa.

Furthermore, according to the above method, a vaginal infection can influence the results of the test. The result of the test may also be erroneous if a long time has passed after the rupture has taken place.

It has also been proposed to detect the rupture of the fetal membrane by utilizing a detectable agent, such as a dye, to stain the amniotic fluid in vaginal secretion samples, and then utilize the color code for diagnosis. Such dyes include Nile blue, acridin orange, bromthymol blue, and nitrasin. Among these dyes, the coloration caused by nitrasin is used to determine an alteration of pH in the vaginal secretion due to the presence of the amniotic fluid (M. L. Friedman and T. W. McElvin, supra). This approach is inconvenient in use and also possesses the same disadvantages as the crystallization method described earlier.

It has recently been proposed to detect the rupture of fetal membranes on the basis of an immunochemical analysis of the proteins contained in the amniotic fluid. Immunochemistry is the branch of science that deals with the chemical changes and phenomena of immunity, specifically, the chemistry of antigens, antibodies, and their reactions. Immunochemical analysis utilizes the following four protein compounds for the diagnosis of the rupture of fetal membranes: alpha-fetoprotein, prolactin, fibronectin, and total insulin-like growth-factor binding protein 1, see B. L. Rochelson, et al., "Rapid Assay-Possible Application in the Diagnosis of Premature Rupture of the Membranes," in *Obstetr. Gynecol.,* 1983, vol. 62, pp. 414–418; Koninckx, et al., "Prolactin Concentration in Vaginal Fluid: A New Method for Diagnosing Ruptured Membranes." *Br. J. Obstetr. Gynecol.* 1981, vol. 88, pp. 607–610; P. Hellemans, et al., "Preliminary Results with the Use of the Rom-Check Immunoassay in the Early Detection of Rupture of the Amniotic Membranes," *Eur. J. Obstetr. Gynecol. Reprod. Biol.,* 1992, Vol. 43, pp. 173–179; Rutanen, E. M., et al., "Measurement of Insulin-like Growth-Factor Binding Protein-1 in Cervical/Vaginal Secretions: Comparison with the ROM-Check Membrane Immunoassay in the Diagnosis of Ruptured Fetal Membranes," *Clin, Chim. Acta,* 1993, vol. 214, pp. 73–81.

Among the above immunochemical methods, those which are based on the detection of alpha-fetoprotein (AFP) and prolactin (PRL) in vaginal secretions are not satisfactory because the corresponding blood/amniotic fluid ratio of the above proteins varies considerably, i.e., between 1 and 10. In some cases, even higher concentrations of proteins were found in serum than in amniotic fluid.

Experience has shown that tests based on the measurement of AFP and PRL have not been sufficiently reliable. AFP and PRL are present in amniotic fluid in high concentration only during the second trimester (i.e., the second three-month period) of the pregnancy. As pregnancy advances, however, the amniotic/serum ratios for both proteins decreases and varies only from 3 to 4 at term. In other words, these methods are unreliable and require that many variable factors be taken into account.

The same problems are encountered in the case of fetal fibronectin, P. Hellemans, et al. "Preliminary Results with the Use of the ROM-Check Immunoassay in the Early Detection of Rupture of the Amniotic Membranes," *Eur. J. Obstetr. Gynecol. Reprod. Biol.,* 1992, vol. 43, pp. 173–179; C. Lockwood, et al., "Fetal Fibronectin in Cervical and Vaginal Secretions as a Predictor of Preterm Delivery," in *The New England Journal of Medicine,* 1991, v. 325, pp. 669–674. The above ROM-check immunoassay is an immunochemical method based on the detection of fetal fibronectin.

In the study conducted by Rutanen, et al., supra, a ROM-check membrane immunoassay had a false positive rate of 20%; the false negative rate was 9%. Alpha-fetoprotein, prolactin, and fibronectin are also present in the amniotic fluid in high concentrations during the second trimester. However, the amniotic fluid/serum ratios for above proteins decrease as the pregnancy advances; at term, they become equal to 3–4.

All the aforementioned methods which utilize alpha-fetoprotein, prolactin, fibronectin, and total insulin-like growth-factor binding protein 1 are not sufficiently informative for the diagnosis because these substances are also contained in the blood serum, albeit at a significantly lower concentration. Their presence in the vaginal secretion sample taken for the analysis may create information noise which will adversely affect the final results of the analysis. This is especially important if the amount of amniotic fluid in the vaginal secretion sample is small.

The disadvantages of all immunochemical methods described are partially eliminated by relying on a diagnostic method for detecting the rupture of fetal membranes; a test kit employing this method is disclosed in published International Patent Application WO 92/12426 to Eeva-Marja Rutanen, 1992. This method is better than the earlier immunochemical methods in that the blood/amniotic fluid ratio of the proteins selected for analysis by Rutanen varies over the second and third trimesters within a narrower range than in the above methods. Nevertheless, in this case the ratio itself has a relatively high absolute value.

The Rutanen method is based on the use of IGFBP-1 which is present in the amniotic fluid and penetrates into the vaginal secretion sample if there has been a rupture of the fetal membranes.

FIG. 1 schematically illustrates IGFBP-1. As shown, this protein has two binding sites, A and B, for the connection of two growth factors, i.e., insulin-like growth factor 1 (IGF-1) and insulin-like growth factor 2 (IGF-2). The presence of the above two sites was discovered by M. Roghani who showed that two insulin-like growth factor (IGF)-binding proteins are responsible for the selective affinity of IGF-II for cerebrospinal fluid-binding proteins, see Roghani, et al., in *J. Clinical Endocr. Metabol.*, 1991, Vol. 73, pp. 658–666. Roghani, et al., assumes that the N-terminal domain common to IGFBP-1, IGFBP-2, and IGFBP-3 contains binding sites for both IGF-1 and IGF-2, but that the high-affinity binding site for IGF-2 is in fact located also in some other region. These authors suppose that the affinity of binding of IGF-1 and IGF-2 to IGFBP-1 is the same, but that IGFBP-1 has two classes of IGF-binding sites, one of high and one of low affinity for both IGFs.

The factors identified above, i.e., IGF-1 and IGF-2, are proteins which regulate the metabolism of carbohydrates in a human body. They are usually present in the blood. Although IGFBP-1 itself does not directly control carbohydrate metabolism, it functions as a carrier for IGF-1 and IGF-2.

The linkage of IGFBP-1 with IGF-1 and IGF-2 is evidently very strong and stable. S. C. Hodkinson and colleagues have demonstrated that, following administration, IGF-1 and IGF-2 were bound to IGFBP-1 with high affinity in minutes, S. C. Hodkinson, et al., "Metabolic Clearance Rate of Insulin-Like Growth-Factor 1 in Fed and Starved Sheep," in *J. Endocrinol.*, 1987, v. 115, pp. 233–240.

E. Rutanen developed two special monoclonal antibodies MAb 6303 and MAb 6305 which are capable of binding to IGFBP-1. However, these antibodies do not compete with IGF-1 and IGF-2, which also have the capability of being tightly bound to IGFBP-1.

Rutanen applies methods which allow the total amount of IGFBP-1 in the blood and the amniotic fluid to be determined using MAb 6303 and MAb 6305 (FIG. 1). In particular, Rutanen uses a method known as a two-site immunoradiometric assay which is described by F. Pekonen, et al., in *Journal of Immunoassay*, 1989, Vol. 10, pp. 325–337. This method consists of placing a vaginal secretion sample into a sample-holding plate containing one of the two above antibodies. The IGFBP-1 molecule contained in the vaginal secretion sample is attached to the antibody which is present in the holding plate. An "antibody" here is a substance capable of binding to a predetermined site of an antigen. An antigen is any substance eliciting an immunologic response such as the production of an antibody specific for that substance.

A specially-labelled second antibody is then introduced and is connected to another site of the same IGFBP-1 molecule. The labelled antibodies are subsequently measured by methods known in the art, e.g., by means of a radioactive counter.

Thus, the Rutanen method measures the total IGFBP-1 in blood serum and the amniotic fluid and, by using the above procedure, can quantitatively determine the amount of IGFBP-1 in the vaginal secretion samples.

Although Rutanen mentions in her patent application that she has developed a special kit which may be used to carry out her method, in fact the patent application has no description of any test kit, except for the reagents used in the method for measuring the concentration of IGFBP-1. There are no drawings or any other physical description of a kit as a device.

A serious drawback of the diagnostic method proposed by E. M. Rutanen, et al., is that it detects IGFBP-1 in a vaginal secretion sample in a concentration range from 0.5 to 90 ng/ml in women even with intact fetal membranes. Probably, this is because IGFBP-1 is also present in the blood in relatively large concentrations. The concentration of total IGFBP-1 in the blood sera of pregnant women ranges from 58 to 600 ng/ml (median 220 ng/ml); therefore, even small admixtures of serum may cause an increase in the level of IGFBP-1 detected in the sample which is significantly higher than the level of sensitivity (about 0.5 ng/ml) of the Rutanen method. Further, Rutanen assumes that even with the fetal membrane being intact, a trace amount of the total IGFBP-1 is still leaking into the vagina.

This means that, first, the Rutanen method makes it difficult to create a simple qualitative "yes/no" test kit. Second, the method can be realized only by adjusting the signal produced by the label in such a way that a positive result occurs only at high concentrations of IGFBP-1. The Rutanen method also dictates that, prior to analysis, the vaginal samples should be diluted to concentrations which are 10 to 20 times lower.

As Rutanen herself states, if the signal used gives a quantitative result, it can always be interpreted as negative when the concentration of IGFBP-1 in the sample is below the highest known concentration caused by maternal serum. This means that if the rupture is small or in its initial stage, the detection of the IGFBP-1 resulting from such a rupture cannot be taken into consideration, because the Rutanen method does not allow the difference between the IGFBP-1 of the amniotic fluid and that of the blood to be determined.

A common disadvantage of all the methods described above is that they require a significant time for the completion of each test in conjunction with laboratory equipment and skilled personnel. The known methods are designed generally for measuring the presence of IGFBP-1 only in a relatively narrow range of its concentration. In order to broaden this range, multiple attempts to match the concentrations of the sample to the specific range of protein concentrations must be made.

Although various test devices which are based on visual color detection of various antigens are known (see, published European Patent Application 421,294 A2 to E. Osikowic, 1991), a simple test kit suitable for rapidly detecting free IGFBP-1 is unknown.

OBJECTS OF THE INVENTION

It is accordingly an object of the present invention to provide a method for detecting free IGFBP-1 which is accurate, i.e., practically free of misleading results ("false negatives") in determining the presence of ruptures in fetal membranes, produces results which are not the consequence of vaginal infection, is convenient to use, makes it possible to rapidly obtain the results of the tests, makes it possible to conduct the test under outpatient conditions, is reliable in operation, does not depend on the timing of the test during the second and third trimesters of pregnancy, does not depend on the admixtures of blood serum in the vaginal secretion sample, does not depend in practical terms on the amount of amniotic fluid which has penetrated into the sample, allows a simple yes/no determination of the presence of a rupture, does not require any dilution and matching of the sample concentrations prior to measurement, and allows the user to distinguish between the IGFBP-1 of the amniotic fluid and that of the blood.

Another object is to provide a simple, inexpensive, rapidly functioning test device to detect the presence of ruptures of the fetal membranes, using vaginal secretion samples.

Yet another object is to provide a method and a device which are equally suitable for low and high concentrations of free IGFBP-1 in the vaginal secretion sample.

A further object is to provide a method for detecting free IGFBP-1 which is accurate and practically error-free.

Still further objects and advantages will become apparent upon consideration of the ensuing description with reference to the accompanying drawings.

DRAWINGS

SUMMARY OF THE INVENTION

Figure 1:
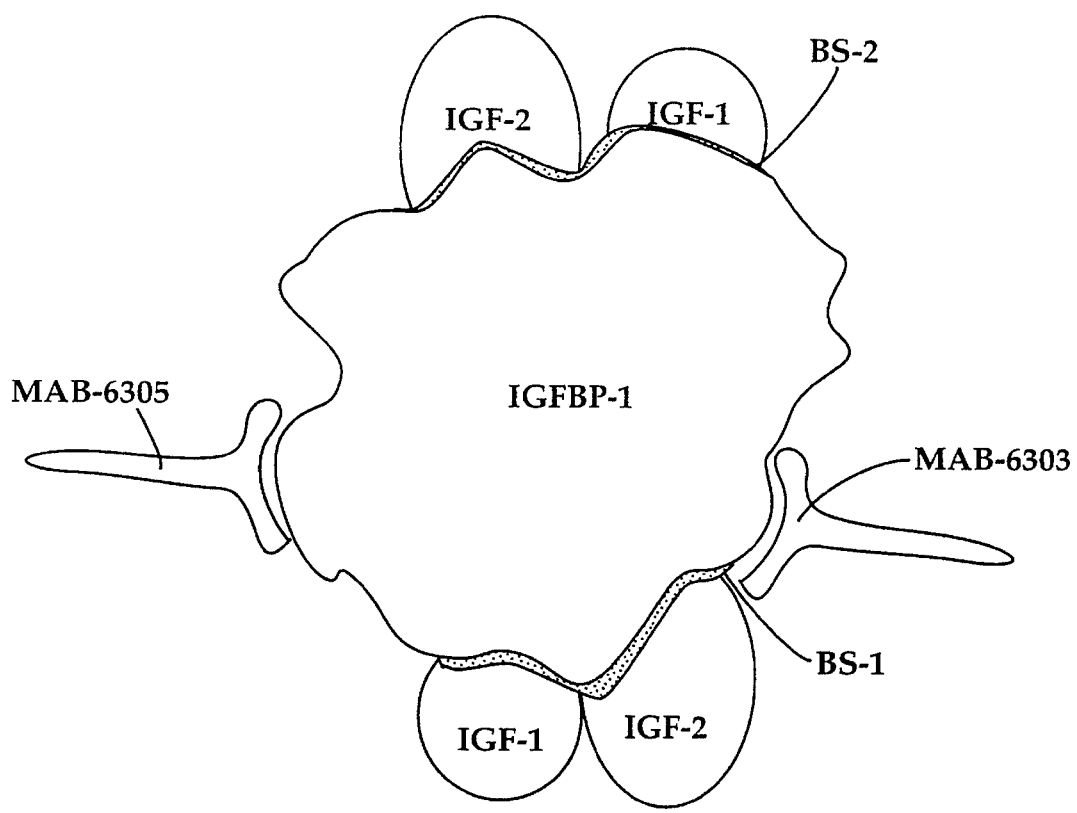
FIG. 1 is a schematic diagram illustrating IGFBP-1 with IGF-1 and IGF-2 attached to their respective binding sites as well as the interaction of antibodies with IGFBP-1, non-competitive with IGF-1 and IGF-2 (prior art).

In accordance with the present invention, we provide a method for detecting the presence of IGFBP-1 in human bodily fluids. This method determines the presence of IGFBP-1 which is free of IGF-1 and IGF-2 and is based on the use of unique monoclonal antibodies which we developed. These antibodies selectively recognize only IGFBP-1 which is free of IGF-1 and IGF-2. Also we provide a one-pad-two-strip test device for carrying out the method.

A device of the invention comprises:

a first medium 22 which contains at least a first labelled antibody;

a first element 36, 24, 28 of a second medium and a second element 34, 26, 30, 32 of the second medium, the first element and the second element of the second medium being attached to the first medium;

the first medium and the second medium being made of porous materials allowing migrations of liquid;

the first element having a test region 28 on a portion of its length which contains a second antibody constantly fixed in the material of the first element;

the second element having a control region 30, 32, the control region consisting of a first part 32 which contains the second antibody and a second part 30 which contains the free insulin-like growth-factor-binding protein 1, the second antibody and the free insulin-like growth-factor-binding protein 1 being constantly fixed in the material of the second element.

DETAILED DESCRIPTION OF THE INVENTION

Detailed Description of the Method

As a result of studies aimed at the development of monoclonal antibodies against IGFBP-1, we discovered that two antibodies obtained in the study are capable of recognizing only those IGFBP-1 molecules which are free of IGF-1 and IGF-2. These monoclonal antibodies will be designated as Mab 1 and Mab 2.

As has been mentioned earlier, IGFBP-1 is a protein which is present in the serum and amniotic fluid of a pregnant women. In fact, IGFBP-1 was at first isolated from the placenta by D. Petrunin in 1977. It was first known as a placenta specific alpha-macroglobulin 1 (PAMG-1), see D. Petrunin, et al., "Immunological Identification of Alpha-1 Macroglobulin of Placenta and Its Content in the Amniotic Fluid," in *Akusherstvo i Ginekologiya*, 1977, N 1, 64–65, Moscow.

Later, an analogous protein was purified from placenta and fetal membranes by Bohn, et al., "Isolierung und Charakterisierung eines Neuen Placentaspezifischen Proteins (PP12)," in *Arch. Gynecol.*, 1980, V. 229, pp. 279–291.

It was observed later that PP12 and IGFBP-1 purified from amniotic fluid have the same N-terminal amino acid sequence, see Povoa, et al., "Cross-Reactions of Serum Somatomedin-Binding Protein in a Radio immunoassay Developed for Somatomedin-Binding Protein Isolated from Human Amniotic Fluid," *Acta Endocrinologica*, 1984, V. 107, pp. 563–570). It was also observed that PP 12 binds IGF-1, Koistinen, et al., "Placental Protein 12 is a Decidual Protein that Binds Somatomedin and Has an Identical N-terminal Amino Acid Sequence with Somatomedin Binding Protein from Human Amniotic Fluid," in *Endocrinology*, 1986, V. 118, p. 1375.

H. Bell, et al., separated endometrial alpha$_1$-globulin (PEG-1) that had an immunochemical identity with PP12 but had two amino acid substituents (amino acid N 11, 12) in the N-terminal peptides of 15 aminoacids. PAMG-1, PP-12 and alpha1-PEG had no distinctions in their physicochemical and immunological properties while PP-12 and alpha$_1$-PEG differed in their amino acid sequence.

In order to identify the isolated protein, applicants conducted a series of measurements for determining the molecular weight of the PAMG-1 obtained. Using an immunoblotting method, applicants measured the molecular weight of PAMG-1 which was equal to 32 kD (kD is an atomic mass unit), see M. N. Boltovskaya, et al., "Histochemical and Clinico-Diagnostic Study of the Placental A-M acroglobulin [PAMG-1] Using Monoclonal Antibodies," in *Bull EXP. Biol. Med.*, 1991, No. 10, pp. 397–400.

The protein studied by Rutanen, et al., had a molecular weight equal to about 25 kD, see Rutanen, et al. *Clinica Chimica Acta*, 1993, pp. 73–81. Earlier she reported more extended weight range, i.e., 25 to 34 kD, see International Patent Application WO 92/12426, supra.

Based on the fact that various proteins of the above type have different molecular weights while having similar structural and functional properties, applicants have assumed that there is a family of proteins which include those mentioned above.

Figure 2:
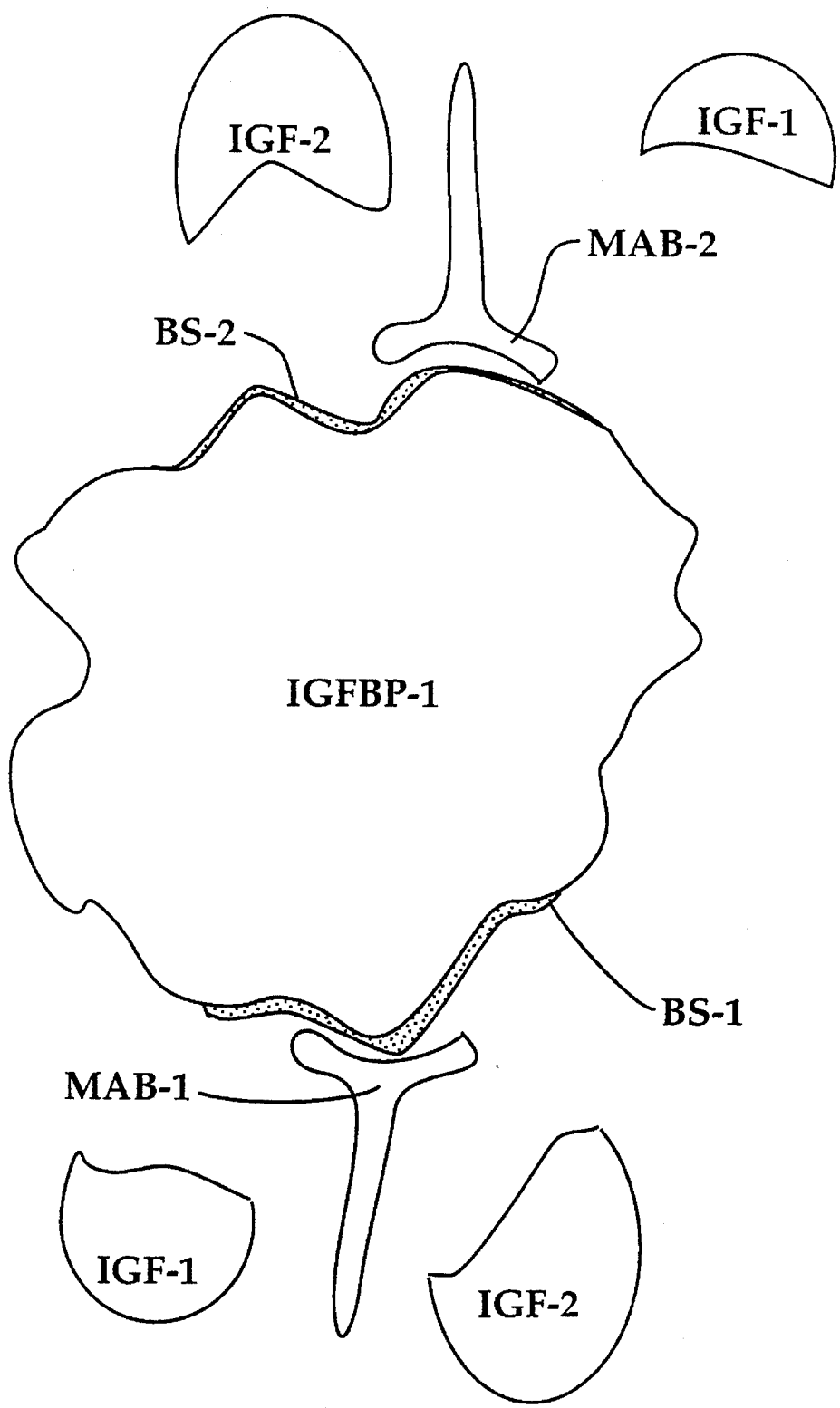
FIG. 2 is a schematic diagram illustrating the principle of the invention where antibodies MAB1 and MAB2 are attached to the binding sites BS-1 and BS-2, IGFBP-1 respectively, and competitively bind thereto with IGF-1 and IGF-2, i.e., where the IGFBP-1 remains free of IGF-1 and IGF-2.

Applicants have recently demonstrated that growth factors IGF-1 and IGF-2 strongly compete with the two aforementioned monoclonal antibodies (antibodies MAB-1 and MAB-2) against the PAMG-1 molecule. This property indicates that PAMG-1 is functionally identical to IGFBP-1. The former two antibodies do not compete with one another with respect to the PAMG-1 molecule. This is schematically illustrated in FIG. 2. This is strong evidence that the binding sites of IGFBP-1 for both antibodies have different structures and thus have a different location on the surface of a single PAMG-1 molecule.

One main principle of the present invention is that antibodies MAB-1 and MAB-2 compete with IGF-1 and IGF-2 for their binding sites located on the PAMG-1 molecule.

This finding will now be substantiated by the following description with reference to Roghani et al., supra, and to Hodkinson et al., supra.

The following study was aimed at revealing the competition between the antibodies Mab-1 and Mab-2, on the one hand, and IGF-1, IGF-2, on the other hand, and was conducted using the ELISA (Enzyme-Linked Immunosorbent Assay) procedure.

First, Mab 1 was adsorbed on plate wells. A solution of PAMG-1 (20 ng/ml) was added to each well. The plate was incubated for 60 minutes at room temperature, using a shaker. After intensive washing of the plate wells, IGF-1 (200 ng/ml, Calbiochem.), or IGF-2 (1 mg/ml, Calbiochem.), was added to different wells. After 60 minutes of incubation and intensive washing of the wells, a conjugate of Mab 2 with peroxidase was added to each well. After 60 minutes of incubation and intensive washing of the wells, a solution of orthophenylendiamine and $H_2O_2$ were added to each well and the intensity of staining was measured using a spectrophotometer.

At the next stage, the same experiments were repeated, only the other way about: using Mab 2 for adsorption on the wells and using the conjugate of Mab 1 with peroxidase at the penultimate step of the reaction. IGF-1 inhibited the Mab 1-PAMG-1 binding by 45% and the Mab 2-PAMG-1 binding by 40%. IGF-2 inhibited the former by 49% and the latter by 69%. Thus, we have discovered that the binding properties of these aforementioned antibodies are unexpectedly strongly competitive to those of IGF-1 and IGF-2.

In order to carry out our method, we had to know the concentrations of free IGFBP-1 both in the blood serum and in the amniotic fluid. These concentrations were measured using the pair of monoclonal antibodies Nos. 1 and 2. The concentration can be measured by any method known in the art of immunochemistry. One such method, known as ELISA, was used by Boltovskaya, et al., supra.

The measurements obtained using the ELISA procedure showed that, apart from some irregular and rare data, in the second and third trimesters of pregnancy, the highest concentration of free IGFBP-1 in the sera of women with an uncomplicated pregnancy was equal to about 35 ng/ml, with an average value of about 21 ng/ml, see Table 1. The concentration of the same IGFBP-1 in the amniotic fluid was 1000 times higher, see Table 2.

TABLE 1

Concentration of free IGFBP-1 in the sera of pregnant women (ng/ml)

| Second trimester (13–25 weeks of gestation) | | | Third trimester (26–40 weeks of geatation) | | | | |
|---|---|---|---|---|---|---|---|
| 24 | 17 | 35 | 25 | 15 | 40 | 6 | 28 | 25 |
| 19 | 15 | 10 | 19 | 21 | 15 | 42 | 32 | 27 |
| 30 | 10 | 39 | 15 | 12 | 11 | 31 | 24 | 40 |
| 25 | 12 | 46 | 5 | 11 | 38 | 40 | 22 | 35 |
| 14 | 22 | 22 | 7 | 30 | 25 | 30 | 17 | 25 |
| 14 | 31 | 27 | 19 | 3 | 12 | 32 | 13 | 26 |
| 27 | 13 | 27 | 21 | 6 | 33 | 30 | 15 | 20 |
| 8 | 38 | 36 | 12 | 12 | 31 | 31 | 12 | 23 |
| 19 | 31 | 12 | 9 | 20 | 40 | 13 | 20 | 35 |
| 15 | 20 | 39 | 22 | 6 | 24 | 30 | 17 | 17 |
| 16 | 40 | 19 | 13 | 15 | 25 | 17 | 16 | 17 |
| 12 | 18 | 25 | 8 | 3 | 33 | 25 | 8 | 15 |
| 17 | 11 | 35 | 8 | 11 | 17 | 16 | 22 | 12 |
| 17 | 40 | 28 | 19 | 7 | 26 | 14 | 20 | 25 |
| 7 | 27 | 17 | 7 | 17 | 30 | 5 | 10 | 8 |
| 16 | 27 | 20 | 6 | 10 | 14 | 32 | 30 | 32 |
| 7 | 14 | 19 | 5 | 9 | 40 | 40 | 32 | 28 |
| | | | 8 | 10 | 45 | | 30 | 35 |
| N = 55 | | | N = 107 | | | | | |
| Range 7–46 ng/ml | | | Range 3–45 ng/ml | | | | | |
| M ± m = 21.58 ± 1.33 | | | M ± m = 20.52 ± 1.03 | | | | | |

In the above table, N stands for the number of measurements, M is the arithmetic mean, and m is the root-mean-square value.

TABLE 2

The concentration of free IGFBP-1 in amniotic fluid
during the second and third trimesters of gestation Free IGFBP-1 (ng/ml)

| | | |
|---|---|---|
| 1680 | 1800 | 1200 |
| 8000 | 26000 | 8000 |
| 6000 | 25000 | 30000 |
| 1000 | 20000 | 6000 |
| 1200 | 100000 | 10000 |
| 20000 | 5000 | 12000 |
| 1000 | 4500 | 20000 |
| 8000 | 12000 | 4000 |
| 250000 | 30000 | 10000 |
| 12000 | 12500 | 7000 |
| 250000 | 25000 | 180000 |
| 6000 | 50000 | |
| 15000 | 80000 | |
| 27000 | 9000 | |
| 5200 | 40000 | |
| 10000 | 41000 | |
| 12000 | 8000 | |
| 4000 | 8000 | |

N = 47
Range - 1000–250000
M ± m = 25742 ± 6604.6

N, M, and m are the same as defined above.

As can be seen from Table 2, in 8% of all patients studied, the concentration of free IGFBP-1 was 4000 ng/ml or lower.

This difference in the free IGFBP-1 concentration between blood and amniotic fluid, on the one hand, and a very low concentration of free IGFBP-1 in serum, on the other hand, allows very low concentrations (5–10 ng/ml) of free amniotic IGFBP-1 in vaginal secretions to be detected as a result of ruptures of the fetal membrane. However, these differences do not give any positive results if the fetal membranes have not been ruptured.

This is one of the important features of the method of the present invention, because the primary problem in diagnosing the rupture of fetal membranes is to distinguish small amounts of the amniotic fluids from other body fluids which may be present in the vagina.

Having described the statistics of the study the following are sequential steps which constitute the method of the invention.

The method of the invention for the detection of free, i.e., unbound, insulin-like growth factor-binding protein 1 for diagnosing fetal membrane rupture on the basis of the presence of amniotic fluid comprises the following steps:

1. One first provides a first and a second antibody capable of binding to a free insulin-like growth-factor-binding protein 1. The first antibody and the second antibody are immunologically different. The free insulin-like growth-factor-binding protein-1 has a first binding site to which the first antibody is capable of binding and a second binding site to which said second antibody is capable of binding.

2. One of the two antibodies is labelled.

3. A vaginal secretion sample from a pregnant woman is taken. The sample possibly contains amniotic fluid having the free insulin-like growth-factor-binding protein 1.

4. The sample is reacted with either the first or second antibody which binds to its respective binding site.

5. The reaction time is sufficient to cause accumulation of labelled antibodies to a detectable degree, thus obtaining an accumulated labelled antibodies.

6. The presence of labelled antibodies bound to the free insulin-like growth-factor-binding protein 1 is detected by observing the accumulated labelled antibodies and this is used to diagnose the occurrence of fetal membrane rupture.

Figure 3:
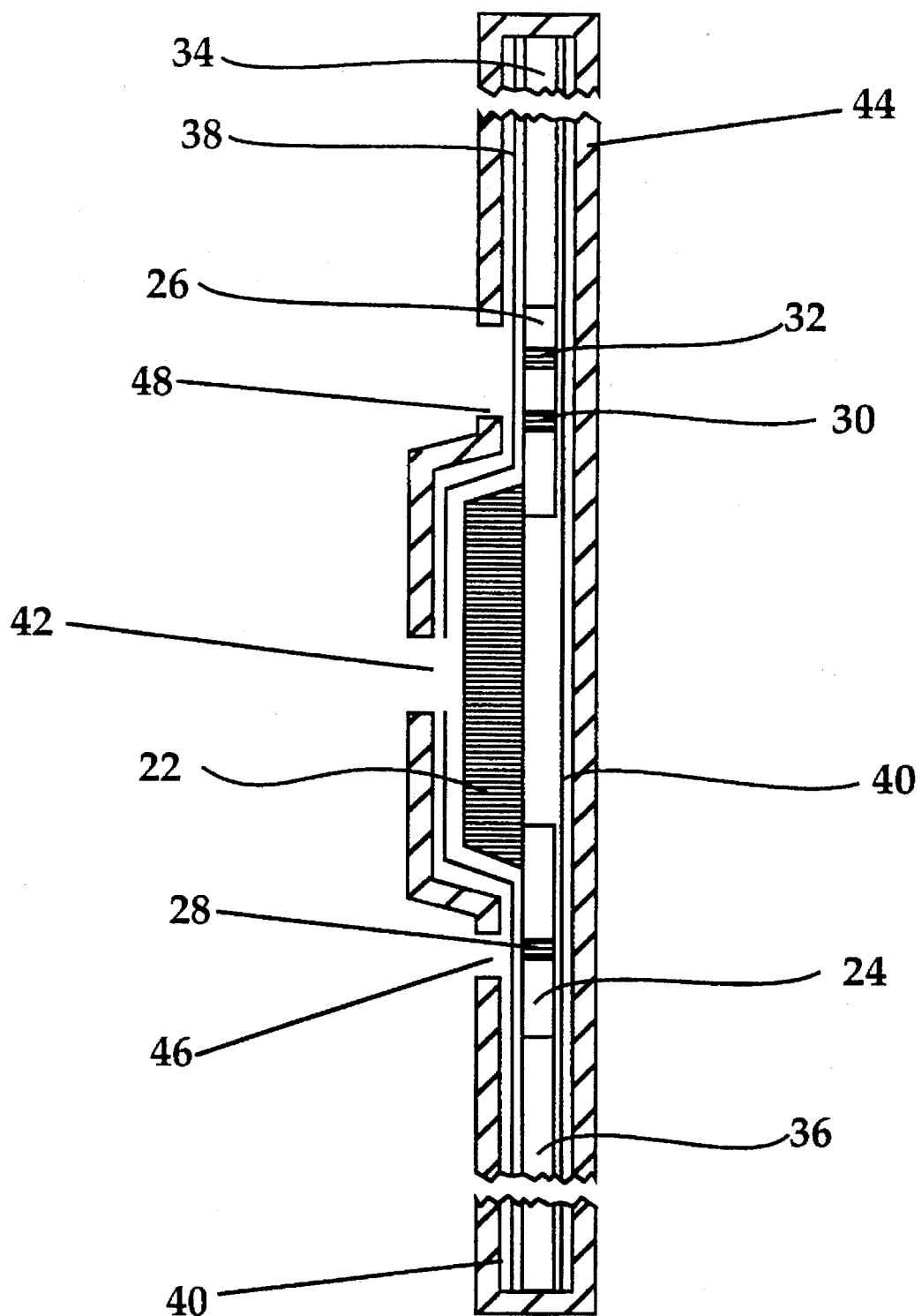
FIG. 3 is a schematic longitudinal sectional view of a device of the invention which may be used to detect the presence of free IGFBP-1 in order to diagnose the rupture of a fetal membrane.
Figure 4:
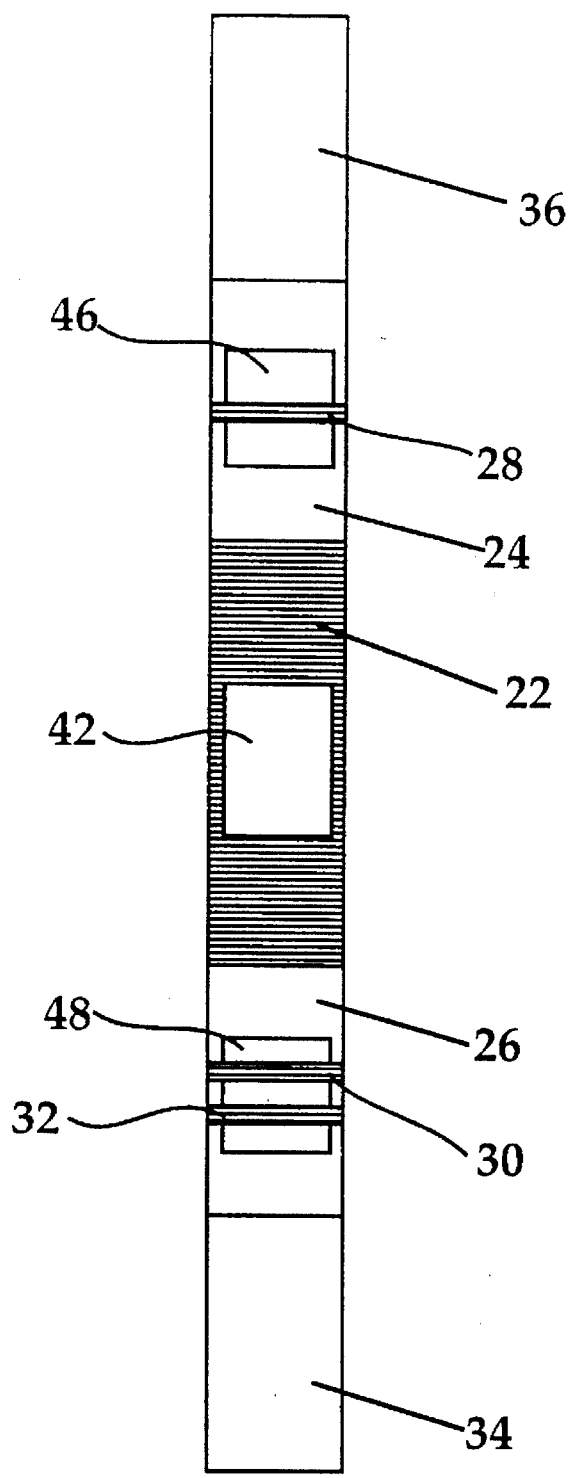
FIG. 4 is a planar view of the device of FIG. 3, the internal structure of the device being seen through a thin transparent protective film.

A one-step device is provided for carrying out the method. A preferred embodiment of this device is shown in FIG. 3, which is a schematic longitudinal sectional view of a device which may be used to detect free IGFBP-1 as a means of diagnosing the rupture of the fetal membranes. FIG. 4 is a plane view of the device of FIG. 1, the internal structure of the device being seen through a transparent protective film.

FIGS. 3 and 4—DESCRIPTION OF THE DEVICE OF THE INVENTION

As shown in FIGS. 3 and 4, the device comprises a strip-like body composed of several sequentially interconnected elements. More specifically, a central part of the device comprises a pad 22 which contains Mab 1 labelled, e.g., by stained particles SP (not shown in the drawings). Pad 22 may be made of a fiberglass tissue. In one specific example, pad 22 had a thickness of 0.25 mm, a width of 7 mm, and a length of 30 mm. The material of pad 22 is porous and permits the migration of various particles which will be described later. Stained particles SP may comprise gold particles having an average dimension within the range of 20 to 40 nm. The labelled Mab(s) 1 are introduced into pad 22, e.g., by impregnating pad 22 with a solution of labelled Mab 1 with subsequent freeze drying.

Connected to the opposite ends of pad 22 in its longitudinal direction are a first nitrocellulose strip, which will be called a test strip 24, and a second nitrocellulose strip, which will be called a control strip 26. Located in an intermediate position of strip 24 is a test region 28 which is arranged transversely to the device over its entire width.

This test region is a portion of nitrocellulose material of strip 24 which is impregnated by Mab 2. Nitrocellulose strips 24 may have a thickness of 0.1 mm, a length of 15 mm, and a width of 7 mm.

Test region 28 may be located, e.g., at a distance of 5 mm from the end of pad 22, and may have a width of 1 mm. Control strip 26 may have the same dimensions as test strip 24 and may contain two transverse control regions 30 and 32, which also may cross the entire width of strip 26 and each have the same width as test region 28. The space between control regions 30 and 32 may be about 1 mm. Control region 32 is identical to test region 28, while control region 30 is impregnated with free IGFBP-1.

Mab 2 and free IGFBP-1 may be introduced into respective nitrocellulose strips 24 and 26 by contact method, e.g., with the use of a dosing drawing-pen-type contact device where the solution is used instead of ink.

Filter paper strips 34 and 36 are connected to the distal ends of nitrocellulose strips 24 and 26. These strips are identical and may have a thickness of 0.2 mm, a width of 7 mm, and a length of 15 mm. Thus, the overall length of the device will be 90 mm.

In order to protect the device from contamination, lateral inflow effect, etc., the entire surface of the device is coated from both sides with protective films 38 and 40, e.g., a conventional thin transparent adhesive tape.

For the introduction of a sample of vaginal secretions, an aperture 42 is provided on the front side of the device in protective film 38.

The device may be enclosed in its entirety into a rigid or semi-rigid casing 44 which closes the front, rear, and sides of the device (with the exception of aperture 42), in order to provide additional mechanical and chemical protection of the device. Casing 44 may be made of plastic such as polycarbonate. For additional clarity of the drawings, casing 44 is shown only in FIG. 3. Casing 44 can be made of transparent or non-transparent plastic. In the event an opaque or semi-transparent plastic is used, casing 44 may be provided with windows 46 and 48 to allow visual observation of the conditions of test region 28 and control regions 30 and 32, respectively.

FIGS. 3–9—OPERATION OF DEVICE OF THE INVENTION

The operation of the device of FIGS. 3 and 4 will now be described in greater detail, with reference to additional drawings illustrating immunochemical interactions which occur within the components of the device during sample analysis.

When it is necessary to test the condition of a patient for the presence of ruptured fetal membranes, a sample of vaginal secretion may be taken by a conventional method and a sample of about 50 to 100 µl is introduced into pad 22 through aperture 42. The sample can be introduced by using pipette, syringe, or any other suitable device (not shown in the drawings).

Figure 5:
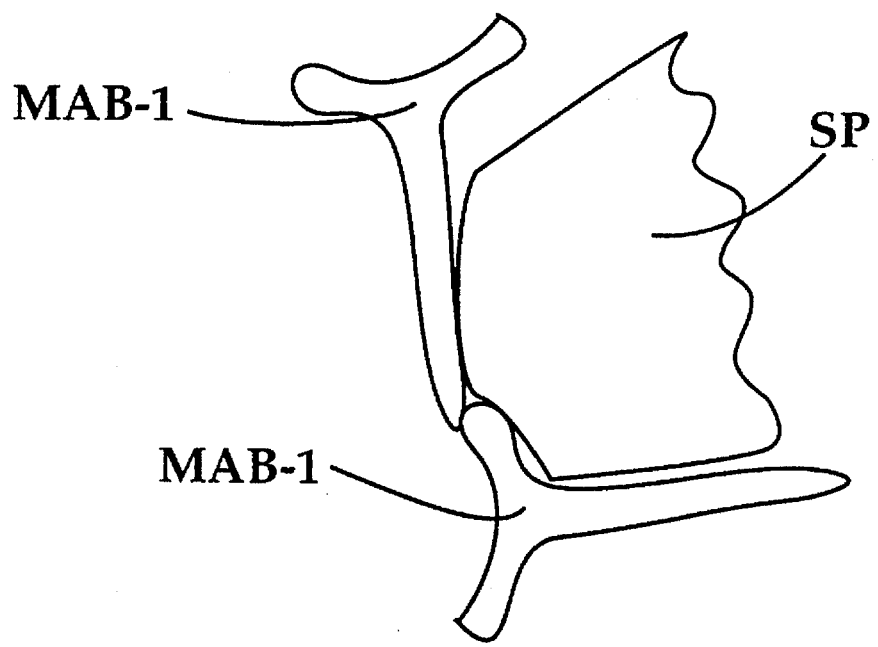
FIG. 5 shows a labelled monoclonal antibody 1 which consists of several antibody molecules attached to a labelling staining particle in a pad of the device of FIG. 3.

If a rupture is present, the sample will contain free IGFBP-1. As has been mentioned, pad 22 contains labelled Mab 1 the intact condition of which is schematically shown in FIG. 5. As shown in this drawing, labelled Mab 1 consists of several antibody molecules attached to label SP.

Figure 6:
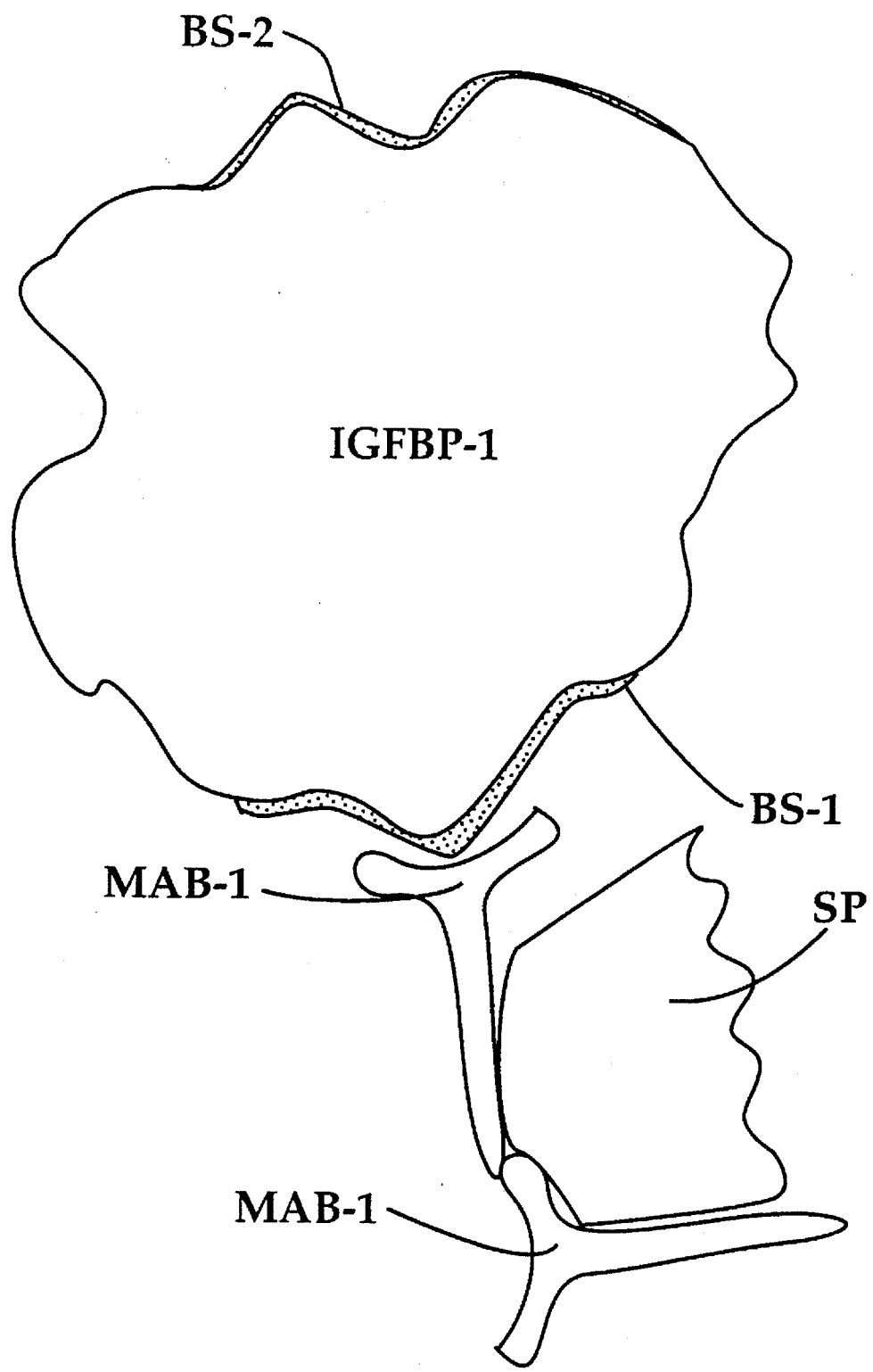
FIG. 6 shows the labelled monoclonal antibody 1 of FIG. 5 attached to its respective binding site 1 free of IGFBP-1.

As soon as the sample is introduced into pad 22, free IGFBP-1 will specifically bind to labelled Mab 1 by its specific binding site BS 1, as shown in FIG. 6.

The complex consisting of SP, Mab 1, and free IGFBP-1 will then migrate through the material of pad 22 toward the nitrocellulose strips. This movement occurs simultaneously in both directions, which essentially reduces the test time as compared to known one-pad one strip devices. However, for ease of the description, the processes which occur in the test device will be considered separately in strips 24 and 26.

Figure 7:
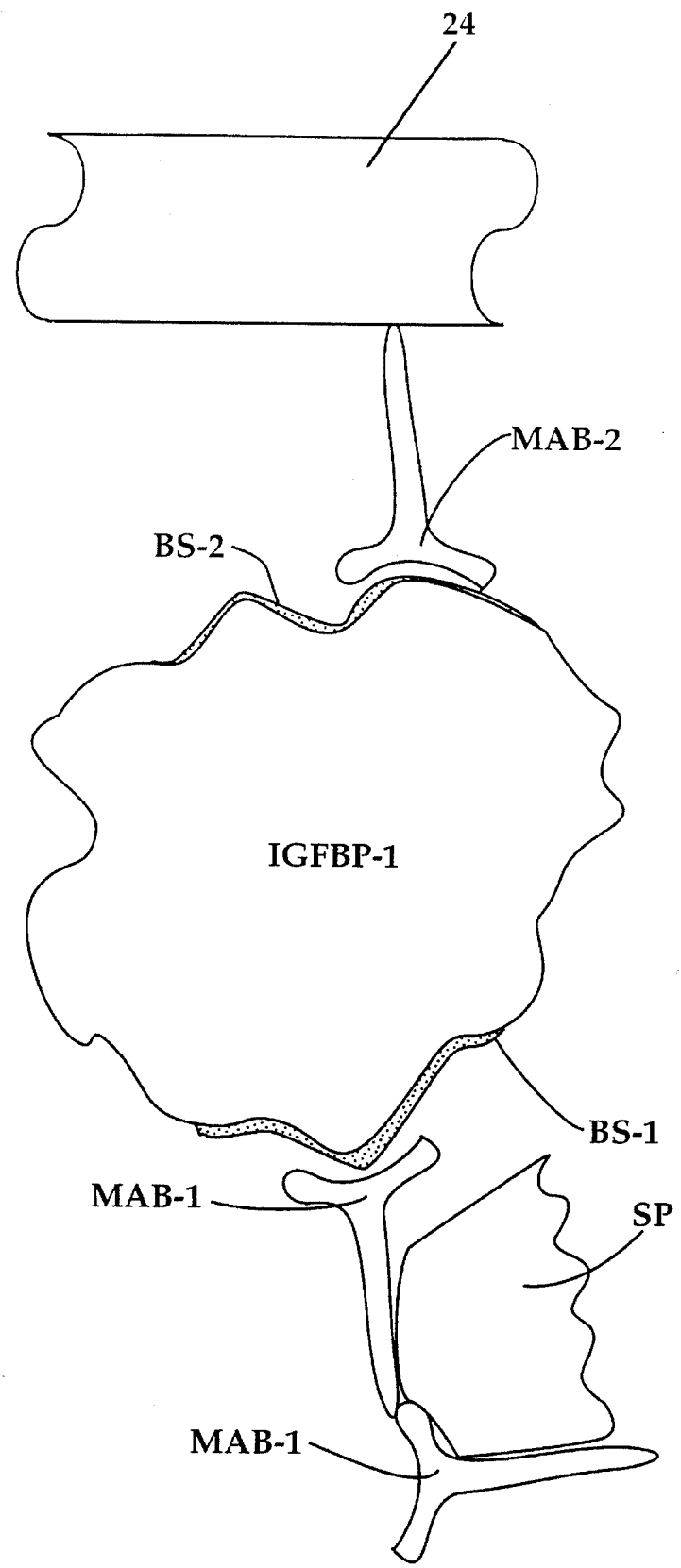
FIG. 7 shows a complex of FIG. 6 which is attached to a second monoclonal antibody which is stationary, bound to a solid phase such as the material of a nitrocellulose strip in the test region of the device of FIG. 3.

When the above complex reaches nitrocellulose strip 24, it continues the movement toward test region 28. When it reaches test region 28, the complex consisting of Mab 1, SP, and free IGFBP-1 binds to Mab 2 which is present in test region 28 by being stationarily attached to the material of nitrocellulose strip 24. This is shown in FIG. 7. The complex is attached to Mab 2 through its specific binding site BS 2 and is captured against further movement. Within 5 to 10 minutes the stained particles SP are accumulated in such an amount that they become distinctly visible to a naked eye in the form of a dark line (not shown). This is used as a qualitative indication of the presence of rupture in the fetal membrane.

Figure 8:
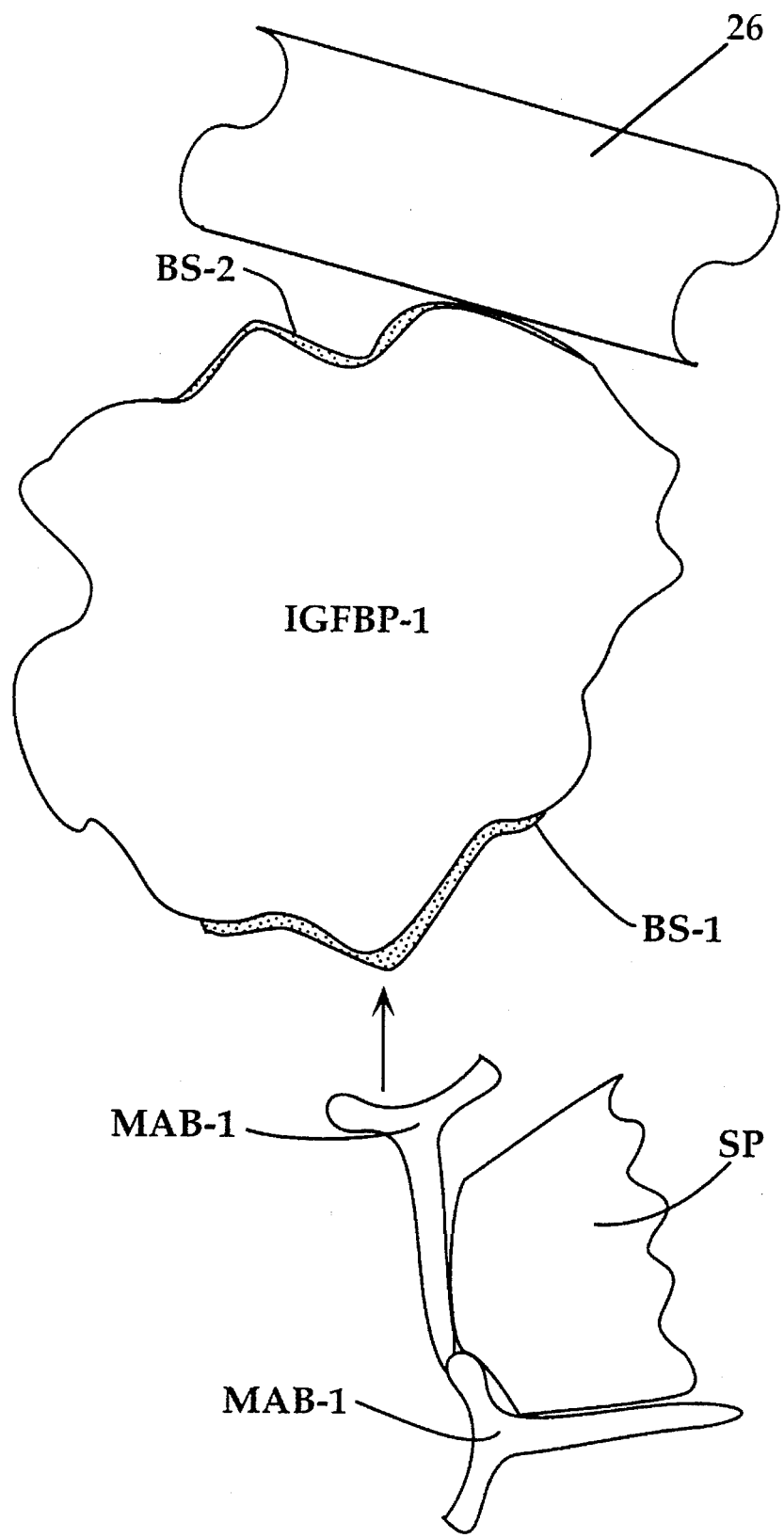
FIG. 8 illustrates the same complex of FIG. 5 in its movement toward free IGFBP-1 fixed to a nitrocellulose strip of a control region.

As far as the function of control regions 30 and 32 is concerned, two scenarios are possible. First assume that the sample does not contain free IGFBP-1, or contains it in a very small amount, e.g., about 10 to 40 ng (i.e., $10^{-9}$ to $40^{-9}$ g). Labelled Mab 1, which is free of IGFBP, will migrate toward test region 28 (FIG. 3). Simultaneously it will migrate toward control regions 30 and 32 (FIG. 8).

Figure 9:
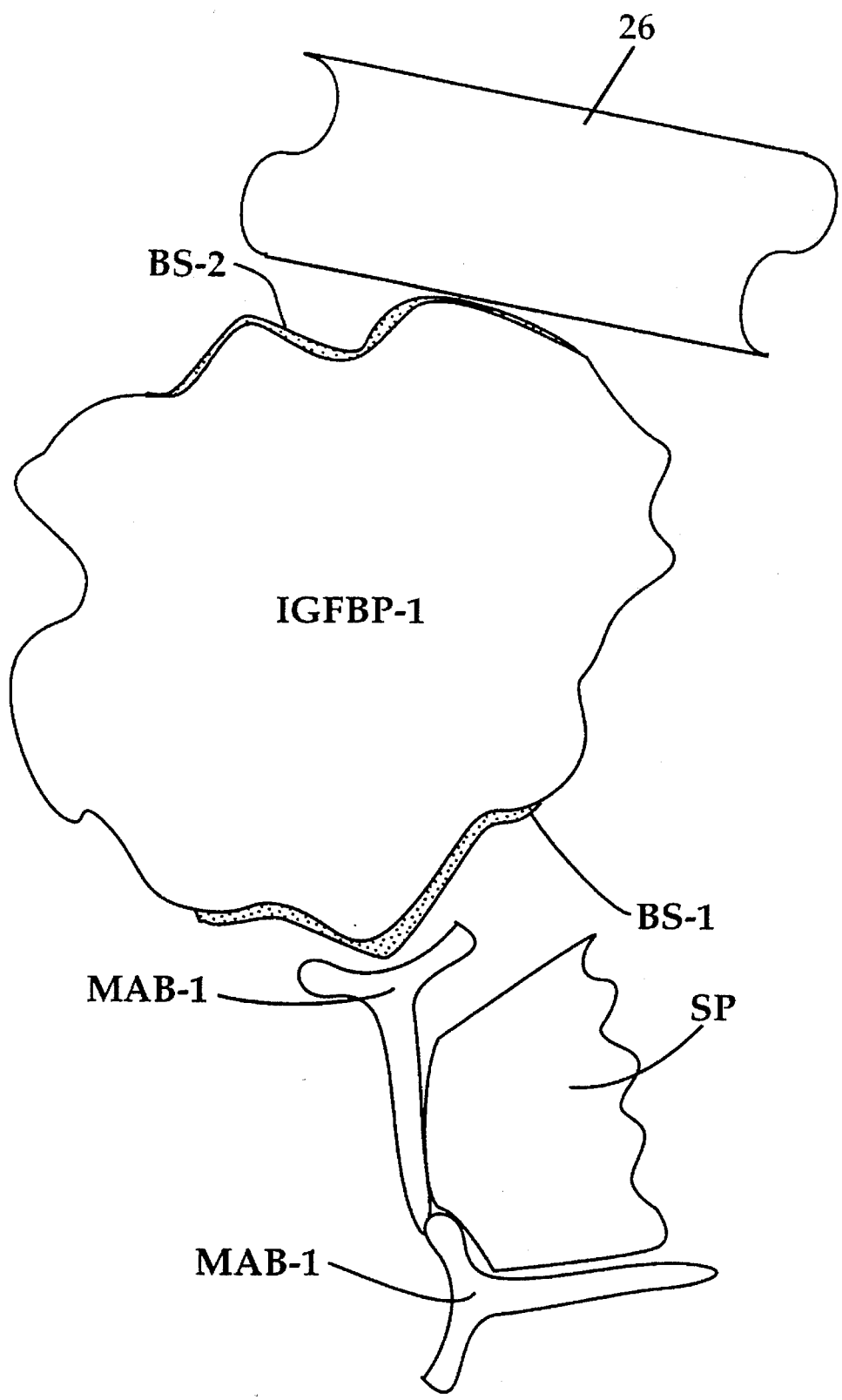
FIG. 9 shows the same complex as in FIG. 8 attached to the respective binding site of free IGFBP-1.

In the case of the first scenario, i.e., the sample is free of free IGFBP-1, or contains only a small amount thereof, labelled Mab 1 will attach to biding site BS 1 of the free IFGBP-1 molecule which has been connected to nitrocellulose material of strip 26 (FIG. 9). As this process continues, the accumulated stained particles SP connected to Mab 1 will be visible to a naked eye as a colored line.

The second scenario corresponds to the presence of free IGFBP-1 in the vaginal secretion sample in significant quantities. Control region 32 is identical to test region 28 and control region 30 does not present a barrier for the complex consisting of free IGFBP-1 with labelled Mab 1 which is overloaded with free IGFBP-1.

Thus the results will be the same as described with reference to test region 28. In other words, the second control region, i.e., control region 32, will be colored and visible, thus proving that the test device is operative and is suitable for use.

Experimental analysis shows that a very high concentration of free IGFBP-1 in a sample may decrease the staining of both the testing and control regions. This is because the speed of migration of the concentrated free IGFBP-1 exceeds the speed of migration of free IGFBP connected to labelled Mab 1. To prevent such an effect, nitrocellulose strip 24 and nitrocellulose strip 26 contain non-labelled Mab 1 for filtering free IGFBP-1 not bound to the labelled Mab 1. This non-labelled Mab 1 is contained on portions of the lengths of strips 24 and 26 between pad 22 and test region 28 and between pad 22 and control region 30.

The test device of the above type (i.e., a one-pad-two-strip system) makes it possible to detect free IGFBP-1 in a wide range of concentrations of free IGFBP-1 in the sample. This is achieved due to the fact that, in the device of the invention, the complex of free IGFBP-1 with labelled Mab 1 does not pass through a test region (which is an indispensable condition of any one-pad-one strip system known to the inventors). This is an important feature, because in the case of a high concentration of free IGFBP-1, its accumulation in the test region of the one-strip system will sharply decrease the staining ability of the positive control region containing free IGFBP with labelled Mab 1.

As far as low concentrations are concerned, the device of the invention is very sensitive even to minute concentrations of free IGFBP-1 (about 5 ng/ml) in the sample. This is because the device has a second strip which operates from the same sample as the first one and which contains a second control region having free IGFBP-1. This second control region will be colored only in the case the concentration of free IGFBP-1 in the sample is low. This is because, in the latter case, a significant amount of Mab 1 will remain free, i.e., not captured by free IGFBP-1 contained in the sample.

EXAMPLES

The method of the invention and the accuracy of its use for diagnosing the rupture of fetal membranes by means of the device of the invention will now be described with reference to practical examples. These examples cover quantitative and qualitative evaluations of the results of detection.

In both cases, the same group of 71 pregnant women was examined and tested with the device of the invention. The device of the invention was used as a qualitative procedure, while the quantitative analysis was performed using the ELISA technique.

The accuracy of the diagnosing was evaluated in terms of sensitivity, prediction value, and specificity.

Sensitivity was measured as a ratio of number of patients with true positive results of the test to the sum consisting of the number of patients with true positive plus the number of patients with false negative results. Here, the number of patients with true positive results means that for these patients the positive result obtained with the use of the device coincides with that obtained by the clinical analysis. The false negative results means that the test gave negative results where the clinical analysis showed the rupture.

Prediction value was determined as a ratio of the number of patients with true positive results of the test to the number of patients which corresponded to the sum of patients with true positive and false positive results. The results were considered true negative if the results of the tests were negative and the clinical analysis confirmed the rupture.

Specificity was determined as a ratio of the number of patients with true negative results to the total number of patients having both true negative and false positive results.

QUALITATIVE PROCEDURE

The device used in the test was the one shown in FIG. 3, with all the features inherent to the preferred embodiment described above. More specifically, pad 22 contained labelled Mab 1 in a freeze-dried state, test region 28 contained Mab 2, control region 30 contained free IGFBP-1, and control region 32 contained Mab 2. Mab 1 was labelled with gold particles having dimensions within the range of 20 to 40 nm. Pad 22 had a thickness of 0.25 mm, a width of 7 mm, and a length of 30 mm. The material of pad 22 was fiberglass fabric. Test strip 24 had a length of 15 mm and a thickness of 0.1 mm. It was made of nitrocellulose. Test region 28 was located at a distance of 5 mm from the end of pad 22 and had a width of 1 mm. Control strip 26 had the same dimensions as test strip 24 and contained two transverse control regions 30 and 32, having the same width as test region 28.

The space between control regions 30 and 32 was to 1 mm. Control region 32 was identical to test region 28, while control region 30 was impregnated with free IGFBP-1.

A few drops (50–200 ml) of a vaginal secretion sample were pipetted on pad 22 of the device. After 5–10 minutes the device was inspected by the naked eye. The results were considered positive if test region 28 was stained and if either both or one control region was stained as well. The results were considered negative if at least one of control regions was stained. The device was considered out of order if both test region 28 and control regions 30 and 32 were not stained.

It was assumed that weak staining of test region 28 corresponded to concentrations of free IGFBP-1 from 5 to 15 ng/ml.

The results of the test conducted with the entire group of patients are given in Table 3.

For the qualitative method, the table shows the following: true positive –35; true negative –33; false positive –1; and false negative –2.

As an example, calculation of sensitivity, prediction value, and specificity were conducted. The results were the following:

| | |
|---|---|
| Sensitivity | 95% |
| Prediction value | 97% |
| Specificity | 97%. |

TABLE 3

Detection of the free IGFBP-1 in vaginal secretion samples in patients with clinically verified diagnosis of fetal membrane rupture. The samples were taken at gestation of 20–34 weeks.

| Patient No. | Free IGFBP-1 strip test (+, −) | IGFBP-1 (ng/ml) ELISA test | Diagnosis of rupture in clinical (yes, no, suspition) | Patient No. | Free IGFBP-1 strip test (+, −) | IGFBP-1 (ng/ml) ELISA test | Diagnosis of rupture in clincial (yes, no, suspition) |
|---|---|---|---|---|---|---|---|
| 1 | − | 0 | no | 36 | + | 3.5 | suspition |
| 2 | + | 30 | yes | 37 | + | 2.5 | yes |
| 3 | + | 250 | yes | 38 | + | 500 | yes |
| 4 | + | 10 | yes | 39 | + | 9 | yes |
| 5 | + | >500 | yes | 40 | − | 0 | no |
| 6 | − | 0 | no | 41 | − | 0 | no |
| 7 | − | 0 | no | 42 | − | 0 | no |
| 8 | − | 0 | no | 43 | − | 0 | no |
| 9 | − | 0 | no | 44 | + | 3840 | yes |
| 10 | − | 0 | no | 45 | + | 26 | yes |
| 11 | + | 120 | yes | 46 | − | 0 | no |
| 12 | + | 20 | yes | 47 | + | 12 | yes |
| 13 | + | 1000 | yes | 48 | − | 0 | no |
| 14 | + | 1000 | yes | 49 | − | 0 | no |
| 15 | + | 18 | no | 50 | + | 8 | yes |
| 16 | − | 0 | no | 51 | − | 0 | no |
| 17 | − | 0 | no | 52 | + | 1000 | yes |
| 18 | − | 0 | no | 53 | + | 15 | yes |
| 19 | − | 0 | no | 54 | − | 0 | no |
| 20 | − | 0 | no | 55 | − | 0 | no |
| 21 | − | 0 | no | 56 | − | 0 | no |
| 22 | + | 240 | yes | 57 | − | 0 | no |
| 23 | + | 100 | yes | 58 | − | 12 | yes |
| 24 | − | 0 | no | 59 | (+/−) | 5 | suspition |
| 25 | − | 7.5 | yes | 60 | + | 1000 | yes |
| 26 | − | 0 | no | 61 | − | 0 | no |

TABLE 3-continued

Detection of the free IGFBP-1 in vaginal secretion samples in patients with clinically verified diagnosis of fetal membrane rupture. The samples were taken at gestation of 20–34 weeks.

| Patient No. | Free IGFBP-1 strip test (+, −) | IGFBP-1 (ng/ml) ELISA test | Diagnosis of rupture in clinical (yes, no, suspition) | Patient No. | Free IGFBP-1 strip test (+, −) | IGFBP-1 (ng/ml) ELISA test | Diagnosis of rupture in clincial (yes, no, suspition) |
|---|---|---|---|---|---|---|---|
| 27 | + | 100 | yes | 62 | + | 75 | yes |
| 28 | + | 200 | yes | 63 | + | 30 | yes |
| 29 | + | 80 | yes | 64 | − | 0 | no |
| 30 | + | 14 | yes | 65 | + | 7000 | yes |
| 31 | − | 0 | no | 66 | + | 20000 | yes |
| 32 | − | 0 | no | 67 | + | 22000 | yes |
| 33 | − | 0 | no | 68 | + | 24000 | yes |
| 34 | − | 0 | no | 69 | + | 24000 | yes |
| 35 | − | 0 | no | 70 | + | 16000 | yes |
|   |   |   |   | 71 | + | 14000 | yes |

QUANTITATIVE METHOD

As mentioned above, the quantitative procedure was conducted using ELISA test for determining free IGFBP concentration in vaginal secretion samples.

The ELISA test was carried out as follows:

50 μl of a diluted (⅕) vaginal secretion sample were introduced into wells of a Linbro plate having 96 wells. A Linbro plate is a special plate produced by Linbro Co., for various tests including ELISA test. The wells were sensitized by the second monoclonal antibody (Mab 2) against free IGFBP-1.

In order to plot a calibration curve, a free IGFBP-1 solution was added to eight sensitized wells in the following respective amounts (ng/μl): 100, 50, 25, 12, 6, 3, 1.5, 0.7. The plate was incubated at room temperature in a shaker for 1 hour.

After intensive washing, 50 μl per well of a conjugate of the first antibody (Mab 1) with peroxidase were added into each well for 15 min of incubation at room temperature in a shaker.

The wells were then washed out, and a mixed solution of orthophenylenediamine with $H_2O_2$ were added into each well for 10 min.

The reaction was then stopped by adding 1N $H_2SO_4$, and light absorbance in wells at 492 nm wavelength with the use of a spectrophotometer, Multiscan, a product of Flow Co., U.K.

A calibration curve was plotted using the abscissa axis for optical density units and ordinate axis for concentrations of free IGFBP-1. These curves were used for quantitatively determining the concentration of free IGFBP-1 concentration in vaginal secretion samples located in other wells of the same plate.

The results showed that the sensitivity was 100, the prediction value was 97, and specificity was 97.

A comparison with the results of the tests by known methods which showed that the method of the invention results in much higher accuracy. This is confirmed by Table No. 4 which shows sensitivity, predictive value, specificity, false positive results, and false negative results for the method of the invention, and two most advanced known methods.

TABLE 4

| Indices (%) | Free IGFBP-1 (pres. inv.) | Total IGFBP-1 (compar. ex.)* | ROM-check membrane immuno-assay* |
|---|---|---|---|
| Sensitivity | 95 | 75 | 92 |
| Predictive value | 97 | 97 | 80 |
| Specificity | 97 | 95 | 79 |
| False positive results | 1.4 | 3 | 20 |
| False negative results | 2.0 | 25 | 9 |

*See - Rutanen et al., 1993, Supra

CONCLUSIONS, RAMIFICATIONS, SCOPE

Thus, it has been shown that we have provided a diagnostic method for detecting free, i.e., unbound insulin-like growth factor-binding protein 1 (hereinafter referred to as free IGFBP-1) and to a test device which may be used to detect the ruptures of fetal membranes according to the above method.

The method is free of false results in determining the presence of the ruptured fetal membranes; it produces results which does not depend on vaginal infection; is convenient to use, allowing the results of the tests to be obtained rapidly and under outpatient conditions; it is reliable in operation, is not limited from the standpoint of age of gestation of the fetus (i.e., whether or not the test is being performed in the second or third trimester of pregnancy); it is not influenced by the admixtures of blood serum in the vaginal secretion sample; it does not practically depend on the amount of the amniotic fluid which has seeped into the sample; it allows a simple "yes/no" determination of the rupture; it does not require any dilutions or matching of the sample concentrations prior to measurements; and it allows the difference between the IGFBP-1 of the amniotic fluid and that of the blood serum to be determined. We have also shown a simple, universal, inexpensive, rapidly functioning test kit which may be used to detect the presence of fetal membrane ruptures, using vaginal secretion samples. The method and the device are applicable both for low and high concentrations of free IGFBP-1 in the vaginal secretion sample.

Although the method and device have been shown and described in the form of specific embodiments, these embodiments, their parts, materials, and configurations have been given only as examples, and that other modifications of the system are possible. For example, the Elisa test used for quantitative determination of free IGFBP-1 can be replaced by other methods known in the field of immunochemistry, such radioimmunoassay. The staining particles may be other than those listed. The test device was illustrated in the form of a strip, although it may have any other configuration. Strips 24 and 26 were described as being made of nitrocellulose, but they may equally be made of other porous materials than fiberglass fabric, such as porous plastic. Pad 22 can be made of other materials than glass fiber fabric, such as porous plastic. The device was described with reference to specific dimensions. It is understood that these dimensions are given as an example and do not limit the scope of the invention. Although the entire method and device relate to free IGFBP-1, the principle of the method and the structure of the device can be employed for qualitative determination of the presence of any other protein in any medium, and in a very wide range of concentrations.

Therefore, the scope of the invention should be determined, not by the examples given, but by the appended claims and their legal equivalents.

What we claim is:

1. A device for detecting free insulin-like growth factor-binding protein 1 (IGFBP-1) in a sample, comprising in fluid communication:

a central porous sample application pad having a first end and an opposing second end, where said central pad (i) contains a mobilizable first monoclonal antibody labeled with a detectable marker, said labeled first monoclonal antibody competing with insulin-like growth factor 1 (IGF-1) and insulin-like growth factor 2 (IGF-2) for specifically binding to said free IGFBP-1, and (ii) having bidirectional migration of said first labeled monoclonal antibody and of a liquid sample therethrough towards both said first and second ends;

a porous test region (i) positioned at said first end and allowing migration of said liquid sample and said labeled first monoclonal antibody therethrough from said central pad into a first absorbent region adjacent said test region, and (ii) containing a second monoclonal antibody immobilized therein, said second monoclonal antibody competing with IGF-1 and IGF-2 for specifically binding to said free IGFBP-1, where said first and second monoclonal antibodies each bind to different sites on said free IGFBP-1;

a porous control region positioned at said second end and allowing migration of said liquid sample and said labeled first monoclonal antibody therethrough from said central pad into a second absorbent region adjacent said control region, said control region comprising (i) a first control area containing said free IGFBP-1 immobilized therein, and (ii) a second control area containing said second monoclonal antibody immobilized therein, where the liquid sample and the labeled first monoclonal antibody can migrate from said first control area to said second control area.

2. The device of claim 1, where said first labeled monoclonal antibody is freeze-dried.

3. The device of claim 1, which further includes a protective film covering at least a portion of said device.

4. The device of claim 3, in which said film covers said central pad and further contains an aperture for sample introduction in the film region covering said central pad.

5. The device of claim 1, further comprising a casing enclosing said device, where said casing possesses an opening above said aperture and observation windows located above said test region and said control region.

6. The device of claim 1, wherein said device further comprises (i) a first porous filter region interposed between said central pad and said test region, and (ii) a second porous filter region interposed between said central pad and said control region, where said first and second filter regions contain said first monoclonal antibody in an immobilized, non-labeled form.

* * * * *